United States Patent [19]

Bilton

[11] 4,447,412

[45] May 8, 1984

[54] ENZYME-CONTAINING DIGESTIVE AID COMPOSTIONS

[76] Inventor: Gerald L. Bilton, 195 Scranton Ct., Zionsville, Ind. 46077

[21] Appl. No.: 462,995

[22] Filed: Feb. 1, 1983

[51] Int. Cl.³ .................... A61K 37/48; A61K 9/42; A61K 9/28

[52] U.S. Cl. .................................... 424/16; 424/32; 424/33; 424/35; 424/38; 424/94

[58] Field of Search ...................... 424/16, 94, 38, 35, 424/32, 33

[56] References Cited

U.S. PATENT DOCUMENTS 3,003,917 10/1961 Beiler et al. ........................... 424/94
3,004,893 10/1961 Martin .................................... 424/94
3,860,702 1/1975 Buell et al. ............................ 424/94
3,932,618 1/1976 Fujii et al. ............................. 424/94
4,079,125 3/1978 Sipos .................................... 424/94

Primary Examiner—Shep K. Rose
Attorney, Agent, or Firm—Kenyon & Kenyon

[57] ABSTRACT

A composition adapted to alleviate the symptons of digestive dysfunction comprising a mixture of coated beads incorporating pancreatic enzymes and proteolytic enzymes and having a gastric acid-resistant coating thereon, said beads being orally-administered in combination with granules comprising a choleretic agent, a hydrochloric acid salt and pepsin.

11 Claims, No Drawings

ENZYME-CONTAINING DIGESTIVE AID COMPOSTIONS

BACKGROUND OF THE INVENTION

The effective functioning of the human digestive process requires the coordinated secretion, delivery and action of a variety of chemical substances.

The stomach secretes gastric juice which is primarily an aqueous solution of hydrochloric acid and pepsin. The acid serves to chemically break down food particles, to activate pepsin, to stimulate pancreatic secretion and to aid iron absorption. Pepsin, a protein produced by the gastric glands, enzymatically digests protein to proteoses and peptones in acid medium, resulting in the further liquefaction of food and reduction of food particle size.

The fluid or semi-fluid stomach contents are then forced into the small intestine. Bile, pancreatic juice and intestinal juice are poured into the small intestine to complete the digestion of food begun in the mouth and stomach. Bile, delivered by the gall bladder, functions to emulsify, digest and to aid the gut absorption of the fatty acids resulting from the enzymatic hydrolysis of fats. Pancreatic juice contains enzymes for digesting proteins, carbohydrates and fats. Among the proteolytic enzymes are trypsin and chymotypsin, which break down larger protein fractions into peptides. Amylose converts starch into maltose and lipase splits fats into fatty acids and glycerin. The pancreas also secretes bicarbonate anions, which neutralize stomach acid and provide an appropriate pH (7-11) for the action of the pancreatic enzymes.

Digestive disorders resulting in the malabsorption of food components may arise from many causes. Cystic fibrosis, chronic pancreatitis, and pancreatic resection may lead to exocrine pancreatic insufficiency, which in turn is characterized by severe steatorrhea, or fecal fat excretion. Stomach cancer and resultant gastrectomy may also cause the disruption of pancreatic function, by reducing the acid secretion necessary for stimulation of pancreatic enzyme production.

Exocrine pancreatic insufficiency is commonly treated by the administration of pancreatic enzyme supplements, often in the form of enteric-coated preparations which resist degradation by stomach acid and pepsin. Other substances such as bile salts, additional proteolytic enzymes, cellulose, hemicellulose and simethicone may be included in varying amounts when the additional goal of treating postprandial abdominal distress symptoms is desired. These symptoms, which include bloating, pain, nausea, and excess intestinal gas production, may be pathological in origin or merely be due to dietary indiscretion or to "nervous indigestion". The composition of a number of these products and their modes of action has been described by D. Y. Graham, *Enzyme Therapy of Digestive Disorders* in *Enzymes As Drugs*, J. S. Holcenberg et al., eds., Wiley-Interscience (1981) at ch. 11.

Despite the numerous products which are, or have been available for the treatment of one or more of the above-described conditions, orally-administrable compositions designed to provide a unified attack on the entire spectrum of digestive disorder symptomology have not heretofore been described.

Therefore, it is an object of the present invention to provide compositions suitable for alleviation of digestive dysfunction due to pancreatic insufficiency, postprandial distress, and the like which are suitable for oral administration.

It is a further object of the present invention to provide compositions which effectively supplement the digestive substances present in both the stomach and small intestine.

Further objects, advantages, and novel features of the present invention will be apparent to those skilled in the art from the following description and appended claims.

BRIEF DESCRIPTION OF THE INVENTION

The objects of the present inventions are attained by orally-administrable compositions which comprise effective amounts of pepsin, a hydrochloric acid source, a source of pancreatic enzymes, a proteolytic enzyme of plant origin and a choleretic agent. The proteolytic enzymes and pancreatic enzymes are adhered to sugar beads which are further coated so as to render them resistant to gastric acid, whereas the other components are formulated so as to be readily released and/or solubilized in the stomach. Thus pepsin and an acid source are available to enhance the digestive action of the stomach juices, bile salts are made available to aid in gut fat absorption, and pancreatic and proteolytic enzymes are provided in an active form to the small intestine to augment the digestion of fats, proteins and starches. These components may be combined with minor amounts of suitable inert adjuvants and tabletted, or encapsulated in powdered form.

DETAILED DESCRIPTION OF THE INVENTION

Pancreatic extracts, particularly porcine and ox pancreatin and porcine pancrelipase, are used in the composition of the present invention to provide a source of the pancreatic enzymes such as lipase, amylase and protease. When delivered in an active form to the small intestine, these pancreatic enzymes act to break down fats, starches and proteins, respectively, into components which can be absorbed by the body. Preferably, pancrease extracts will comprise about 5.0-25% by weight of the present compositions, most preferably 10-20%.

Although the pancreatic extracts employed in the present compositions will possess some degree of proteolytic activity, additional amounts of proteolytic enzymes, such as the plant-derived proteolytic enzymes bromelain, papain, ficin and mixtures thereof are used in the present compositions to optimize their effectiveness in reducing postprandial digestive syndrome and for reducing the symptoms of episeotomy. Bromelain is the preferred proteolytic enzyme to be used in the present compositions, and may comprise about 2.5-15%, preferably 5-10% by weight of the composition.

Choleretic digestants useful in the compositions of the present invention include bile, bile acids and bile salts, with desiccated bile extracts, e.g., ox bile extracts, being preferred. When administered orally, bile salts are absorbed from the intestine and reexcreted by the liver in the bile, thus entering the same cyclic process as endogenous bile salts. They are of value in promoting the absorption of fats and fat-soluble vitamins from the intestinal tract when the normal biliary or pancreatic output is either reduced or absent. Bile salts will preferably comprise about 2.5-15%, preferably 5-10% by weight of the present compositions.

The compositions of the present invention will also comprise about 5-25%, preferably 10-20% of a hydrochloric acid source, preferably as an organic hydrochloride salt such as glutamic acid hydrochloride or betaine hydrochloride. Hydrochloric acid acts in the gastrointestinal tract to activate pepsin, render gastric contents relatively sterile, aid in the secretion of pancreatic juices and allow the absorption of certain inorganic salts. Hydrochloric acid salts are effective in relieving symptoms due to hyperchlorhydria or achlorhydria, conditions which may be genetic or due to gastritis or gastric carcinoma, respectively.

The compositions of the present invention will also include an effective amount of pepsin, preferably as the N.F. grade, although grades of higher activity may also be used. Pepsin acts in the stomach to hydrolyze proteins into polypeptides and amino acids, and thus acts in concert with the bromelain and the pancreatic proteolytic enzymes to restore and maintain the body's amino acid balance. Preferably, pepsin will comprise about 5-25%, most preferably 10-20% of the present compositions.

The above-described active ingredients, preferably will comprise about 40-80%, and most preferably 45-75% by weight of the present compositions before the addition of adjuvants and tabletting.

Since the pancreatic enzymes and the other proteolytic enzymes (i.e., the bromelain or papain) are readily degraded and deactivated under conditions of low pH, they must be incorporated into the present compositions in a manner which will protect them from stomach acid and deliver them rapidly to the small intestine. On the other hand, the pepsin, bile salts and hydrochloric acid salts should be formulated so as to be quickly released in the stomach.

To accomplish these modes of delivery, the pancreatic extract and additional proteolytic enzyme are adhered onto and/or absorbed into digestible beadlets which may be formed of substances such as sugars, starches and the like. The beadlets are sized so as to pass readily through the stomach into the small intestine, i.e., to be carried through and out of the stomach by the normal flow of digestive juices, and are coated so that they will maintain their integrity in the stomach but rapidly disintegrate in the small intestine. Thus, a sugar-starch Nupareil® bead (Specialty Food Products, Pennsauken, N.J.) about 0.1-0.2 mm in diameter will have a coated diameter within the useful range of about 0.3-0.5 mm.

The acid-stable components of the composition are agglomerated and mixed with the coated beadlets and the mixture encapsulated or compressed into tablets with suitable adjuvant fillers, lubricants, and coating materials.

Thus, tablets prepared in the above-described manner will comprise about 35-75%, and most preferably 40-70% by weight of the active ingredients described hereinabove. The pancreatic extracts and additional plant-derived proteolytic enzymes will comprise about 20-75%, preferably about 30-50% by weight of the total active ingredients, and will be adhered to and/or absorbed into digestible beadlets which will, when loaded with enzymes and enteric-coated, comprise about 35-65%, preferably about 45-55% by weight of the finished tablets. If the beadlet-bile-pepsin-acid mix is not tabletted, but is encapsulated, the proportion of coated beadlets in the final composition will be somewhat higher, preferably about 50-70% of the composition. Preferably the pancreas extracts and bromelain (or papain) will be used in about a 2:1 weight ratio.

Any coating composition which will maintain the integrity of the enzyme-treated beads in gastric juice for at least about 1-2 hours may be applied to protect the beads using methods and formulations well known to those of skill in the pharmaceutical coating arts. For example, suitable enteric-coating materials are discussed in Remington's Pharmaceutical Sciences, A. Osol, ed., Mack Pub. Co., Easton, Pa. (16th ed. 1980) at pages 1590-1593, the disclosure of which is incorporated by reference herein. Mixtures of fats and fatty acids are preferred, preferably about a 1:1 to 5:1 mixture of stearic acid and carnauba wax, which is added to the beadlets while they are being sprayed with a food glaze-alcohol solution. The acid-resistant coating will preferably comprise about 5-20% by weight of the finished bead, although the coating should be thinner in cases involving the treatment of patients with extremely low stomach acidity.

A mixture of about 30-50%, preferably 35-45% by weight of a mixture of bile extract, pepsin and an organic hydrochloride salt, preferably in a weight ratio of about 1:2:2 is prepared in the presence of about 15-25% water and about 0.5-5% of a binder (i.e., guar gum).

The resultant mixture is coarse-screened, dried and ground to a particle size of about 0.5-2.0 mm in diameter, or about 10-16 mesh (U.S. Standard Sieve Series). The granules are combined with the coated beads and encapsulated or, optionally, further combined with suitable amounts of filler and lubricant and compressed into tablets. The tablets may be further finish-coated, for example, with zein, wax, and/or sugar. The hereinabove described formulation steps are carried out under conditions resulting in no more than about a 10% loss in the activity of any given enzymatic component, as measured by standard procedures.

Thus, preferred compositions of the present invention will comprise, before the addition of tabletting adjuvants, about 50-70% by weight of enzyme-treated, coated sugar beadlets which have absorbed therein or coated thereon about 10-20% by weight of pancreatin, and about 5-10% by weight of one or more plant proteolytic enzymes.

The beadlets are mixed with about 35-45% of a granulated mixture of bile salt, pepsin and an organic hydrochloride which have been agglomerated in the presence of 0.5-5% of a binding agent. The bile, pepsin and acid are present in weight ranges of about 5-10%, 10-20% and 10-20%, respectively, all weights being expressed as percent of the entire composition.

Preferred composition of the present invention comprise the above-described compositions which have been compressed into tablets in the presence of about 5-15% of a mixture of biologically inert adjuvants comprising lubricants, fillers and coatings.

Acceptable lubricants comprise mixtures of hydrogenated vegetable oils of conventional pharmaceutical grade and fatty acid salts, magnesium stearate, i.e., in about a 2:1 ratio (about 5-10% by weight of the finished tablet).

Fillers such as microcrystalline cellulose, calcium sulfate and sugars may be used, preferably in amounts of about 1-10% by weight of the finished tablets.

A finish coating of zein (whole corn protein; Chicago Specialty, Chicago, Ill.) may further be applied and the tablets buffed if desired.

The invention will further be described by reference to the following detailed example.

A stainless steel coating pan was loaded with 32.5 kg of Nupareil ® sucrose/starch beads and agitation begun. A solution of 5.0 kg of White Lac glaze in 5.0 kg denatured ethanol was prepared and continuously pressure-sprayed onto the beads while 12.5 kg of bromelain and 25.0 kg of pancreatin powder were added to the moving beads. Agitation was continued while a mixture of 3.25 kg of stearic acid and 3.25 kg of carnauba wax were added portion wise to the beads to provide a coating layer. Talc was added as necessary to prevent agglomeration of the beads. Rounded beads were obtained of an average diameter of 0.3-0.5 mm.

A mixture of 12.5 kg ox bile extract, 2.5 kg of pepsin N.F., 25 kg of betaine hydrochloride and 2.5 kg of guar gum was ribbon blended with about 7.5 kg of water to form a dough which was screened (6 mesh) and dried in a hot air oven at 50° C. The resultant granules were ground in a Fitz mill, then dry-screened to a 16 mesh size.

The granules were mixed with the coated beads in the coating pan and blended with 2.5 kg hydrogenated vegetable oil, 3.75 kg of microcrystalline cellulose and 12.5 kg of magnesium stearate. The bead-containing mixture was punched into about 250,000 600 mg tablets on a tablet punch equipped with standard concave (7/16 inch) tooling.

The tablets were then returned to the coating pan and spray-coated with a solution of 7.5 g of zein (1% in ethanol), followed by drying for 1.5 hours and bottling.

Alternatively, the bead-granule mixture is encapsulated in 500 mg gelatin capsules prior to treatment with the lubricants and fillers.

The coated beads present in either the tabletted or encapsulated preparation resisted disintegration in 1.2 N hydrochloric acid stirred at 30 rpm for at least one hour, thus demonstrating the stability of the coating.

It has been reported that 1 or 2 of the tablets, when ingested at mealtime, are effective in relieving the symptoms of postprandial digestive distress.

While certain representative embodiments of the invention have been described herein for purposes of illustration, it will be apparent to those skilled in the art that modifications therein may be made without departing from the spirit and scope of the invention.

I claim:

1. A composition adapted to reduce the symptoms of digestive dysfunction when ingested orally comprising:
    (a) a pancreatic enzyme extract;
    (b) a proteolytic enzyme of plant origin;
    (c) a choleretic agent;
    (d) a hydrochloric acid source; and
    (e) pepsin,
wherein the pancreatic enzyme extract and the proteolytic plant enzyme are adhered to digestible beads, said enzyme-containing beads being further coated so as to maintain their integrity when placed in about 1.2 N aqueous hydrochloric acid for at least one hour, and said coated beads being sized so as to readily pass through the stomach, and said coated beads being mixed with granules comprising the choleretic agent, the hydrochloric acid source and pepsin.

2. The composition of claim 1 wherein the coated beads are about 0.3-0.5 mm in diameter, and the coating comprises about 5-20% by weight of the coated bead.

3. The composition of claim 1 wherein the pancreatic enzyme extract is selected from the group consisting of pancreatin, pancrelipase and mixtures thereof; and the proteolytic plant enzyme is selected from the group consisting of bromelain, papain, ficin and mixtures thereof.

4. The composition of claim 3 wherein the choleretic agent is an ox bile extract, and the hydrochloric acid salt is selected from the group consisting of glutamic acid hydrochloride, betaine hydrochloride and mixtures thereof.

5. The composition of claim 2 wherein said granules are about 0.5-2.0 mm in diameter.

6. The composition of claim 1 wherein the coating comprises a mixture of carnauba wax and stearic acid in a ratio of about 1:1-5.

7. The composition of claim 1 wherein the coated beads comprise about 50-70% by weight of the composition.

8. The composition of claim 2 wherein the pancreatic enzyme extract comprises about 5-25% by weight of the composition, the proteolytic enzyme comprises about 2.5-15% by weight of the composition, the choleretic agent comprises about 2.5-15% by weight of the composition, the pepsin comprises about 5-25% by weight of the composition and the hydrochloric acid source comprises about 5-25% by weight of the composition.

9. A composition adapted to reduce the symptoms of digestive dysfunction when ingested orally comprising:
    (a) about 10-20% by weight of a pancreatic enzyme extract selected from the group consisting of pancreatin, pancrelipase and mixtures thereof;
    (b) about 5-10% by weight of a proteolytic enzyme selected from the group consisting of papain, bromelain, ficin and mixtures thereof;
    (c) about 5-10% by weight of a bile salt;
    (d) about 10-20% by weight of pepsin; and
    (e) about 10-20% by weight of an organic hydrochloride selected from the group consisting of glutamic acid hydrochloride, betaine hydrochloride and mixtures thereof;
wherein the pancreatic enzyme extract and the proteolytic enzyme are adhered to digestible beads, said enzyme-containing beads being further coated so as to maintain their integrity in the stomach upon ingestion, and wherein the coated beads are sized so as to readily pass through the stomach, and said beads being mixed with granules comprising the bile salt, the pepsin and the acid salt.

10. The composition of claim 9 wherein the pancreatic enzyme extract is pancreatin, the proteolytic enzyme is bromelain, the bile salt is ox bile extract and the hydrochloride is betaine hydrochloride.

11. A method of relieving the symptoms of pancreatic insufficiency of postpandrial distress syndrome comprising orally-administering an effective amount of the composition of claim 9.

* * * * *